United States Patent
Boutros

[19]

[11] Patent Number: 6,036,709
[45] Date of Patent: Mar. 14, 2000

[54] OPHTHALMIC INSTRUMENT AND METHOD FOR PREPARING AN EYE FOR LASIK

[75] Inventor: George J. E. Boutros, 7550 220th St., Chanute, Kans. 66720

[73] Assignees: George J. E. Boutros, Chanute, Kans.; Kalil M. Jiraki, Dertoit, Mich.

[21] Appl. No.: 09/178,643

[22] Filed: Oct. 26, 1998

[51] Int. Cl.$^7$ ............................................. A61F 9/00
[52] U.S. Cl. ............................................. 606/166
[58] Field of Search ........................ 606/161, 166, 606/180, 107; 623/4, 5, 6; 351/177, 246

[56] References Cited

U.S. PATENT DOCUMENTS 4,763,651  8/1988  Kaufman et al. ..................... 606/166
5,290,301  3/1994  Lieberman ........................... 606/166

OTHER PUBLICATIONS

Current Model of Hessburg–Barron Vacuum Trephine, Manufactured by Jedmed Instrument Co., St. Louis, Mo. 63129; Dated at Least Before Aug. 1998, Believed Much Earlier.
Old Model of Hessburg–Barron Vacuum Trephine with 2 Concentric Circular Blades. This Instrument has Been out of Manufacture for Years.

*Primary Examiner*—George Manuel
*Attorney, Agent, or Firm*—Peter D. Keefe

[57] ABSTRACT

An ophthalmic instrument and ophthalmic method for preventing epithelium cells from being deposited at the stroma interface during LASIK. The ophthalmic instrument has a base having a flat abutment face, two mutually concentric annular blades upstanding from the abutment face, and a cross-hair for sighting the position of the annular blades. The annular blades have a height of about 50 microns with respect to the abutment face, an inner annular blade thereof is from about 9 mm. to about 9.5 mm. in diameter, and an outer annular blade thereof is about 10.5 mm. in diameter. The ophthalmic method is performed prior to LASIK. The ophthalmic instrument is aligned over the cornea via the cross-hairs and then pressed upon the eye of a LASIK patient so that the annular blades cut into the cornea until the abutment face abuts the cornea and prevents further penetration. The depth of cut of the annular blades is such as to completely cut through the epithelium. The ophthalmic instrument is removed, leaving behind two mutually concentric annular cuts in the cornea, an epithelial ring being located therebetween. Next, an ophthalmic tool, such as for example a delicate forceps or tweezers is used to carefully grasp the epithelial ring and pull it free of the remainder of the cornea. As a result, an annular epithelial void is present on the cornea. Now, a surgeon may commence LASIK and when the flap cut is made, the blade cannot cut epithelium tissue on account of the epithelial void.

17 Claims, 2 Drawing Sheets

OPHTHALMIC INSTRUMENT AND METHOD FOR PREPARING AN EYE FOR LASIK

BACKGROUND OF THE INVENTION

1. Field of the Invention

The present invention relates to ophthalmic surgical procedures for the correction of refractive defect. More particularly, the present invention relates to an ophthalmic refractive correction procedure known as LASIK, wherein a corneal flap is produced thereduring. Still more particularly, the present invention relates to an ophthalmic instrument and method which prepares an eye for LASIK flap procedure to thereby provide minimization of post operative complications of the LASIK flap procedure.

2. Description of the Prior Art

Surgery to correct refractive defect of the eye have been practiced in the ophthalmic arts for a number of years. One currently well known and highly regarded such procedure is known as LASIK. LASIK stands for "laser in situ keratomileusis".

An over view of LASIK involves the following steps: cutting a flap of corneal tissue in front of the pupil, folding the flap out of the way of the underlying cut corneal interface, laser oblating the underlying corneal interface to the patient's refractive prescription, then folding the flap back, whereupon naturally occurring eye suction retains the flap in place.

In order to cut the flap, LASIK involves a device known as a "microkeratome". The microkeratome is placed upon the eye and has an interface which when pressed upon the eye causes flattening of the cornea. The microkeratome has a sliding blade mechanism whereby a surgical blade is slid across the eye to produce the flap. The microkeratome provides for the blade to stop short of severing the flap from the cornea, the connection being referred to as the "hinge". It is the hinge which allows the flap to be safely folded or rolled out of the way for the refractive oblation procedure, and then folded or rolled back without alignment error.

The flap cutting process is quite sensitive to the satisfactory outcome of LASIK. In this regard, the microkeratome flattens the eye prior to the flap cut in order that a uniform thickness flap is produced. The flap cut involves cutting through an outer and inner layer of the cornea to a preset depth. The corneal outer layer is called the "epithelium" and the corneal inner layer is called the "stroma". The epthelium is under 50 microns thick and the flap thickness is about 160 to 180 microns. Accordingly, the flap cutting procedure provides a circular shaped stroma interface between the flap and the remainder of the cornea, and a ring shaped epithelium interface between the periphery of the flap and the remainder of the cornea.

One of the most feared complications of LASIK is that during the flap cutting procedure, some epithelium cells can attach to the blade and become deposited at the stromal interface. Should this occur, when the flap is repositioned these epithelium cells will remain located at the stroma interface. These errant epthelium cells can then develop into inclusion cysts, leading to a variety of adverse symptomatology.

Accordingly, what is needed in the art is prevention of epithelium cells from being deposited at the stroma interface during LASIK.

SUMMARY OF THE INVENTION

The present invention is a ophthalmic instrument and ophthalmic method for preventing epithelium cells from being deposited at the stroma interface during LASIK.

The ophthalmic instrument according to the present invention includes a base having a flat abutment face and two mutually concentric annular blades upstanding from the abutment face. The ophthalmic instrument further has a preferably cylindrically shaped central hollow having a cross-hair for sighting the position of the annular blades. Finally, an external handhold is preferably provided for a surgeon to grasp the ophthalmic instrument with a high level of competency.

In the preferred form the of ophthalmic instrument, the annular blades (an inner annular blade and an outer annular blade) have a height of about 50 microns with respect to the abutment face. The inner annular blade has a diameter of from about 9 mm. to about 9.5 mm. and the outer annular blade has a diameter of about 10.5 mm.

The ophthalmic method according to the present invention is performed prior to LASIK. The ophthalmic instrument is grasped via the handhold by a surgeon, aligned over the cornea via the cross-hairs and then pressed upon the eye of a LASIK patient so that the inner and outer annular blades cut into the cornea until the abutment face abuts the cornea and prevents further penetration. The depth of cut of the inner and outer annular blades is such as to completely cut through the epithelium.

The surgeon removes the ophthalmic instrument from the eye, leaving behind two mutually concentric annular cuts in the cornea, an epithelial ring being located therebetween. Next the surgeon uses an ophthalmic tool, such as for example a delicate forceps or tweezers to carefully grasp the epithelial ring and pull it free of the remainder of the cornea. As a result, an annular epithelial void is present on the cornea.

Now, the surgeon commences LASIK, whereby when the flap cut is made, the blade does not cut epithelium tissue on account of the epithelial void which is located where the epithelial interface would conventionally be produced during LASIK. Accordingly, since there is no epithelium interface, there is no chance for errant epithelium cells from being deposited at the stroma interface during LASIK.

Accordingly, it is an object of the present invention to prevent epithelium cells from being deposited at the stroma interface during LASIK.

It is an additional object of the present invention to provide an ophthalmic instrument which is used prior to LASIK to prepare the cornea for flap cutting.

It is yet another object of the present invention to provide an ophthalmic method using an ophthalmic instrument prior to LASIK, whereby epithelium cells are prevented from being deposited at the stroma interface during LASIK.

These, and additional objects, advantages, features and benefits of the present invention will become apparent from the following specification.

DETAILED DESCRIPTION OF THE PREFERRED EMBODIMENT

Figure 1:
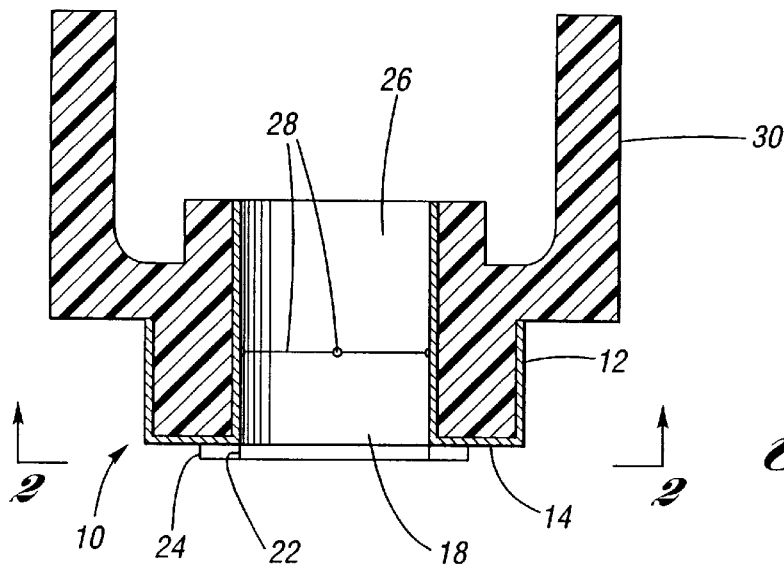
FIG. 1 is a partly cross-sectional view of an ophthalmic instrument according to the present invention.
Figure 2:
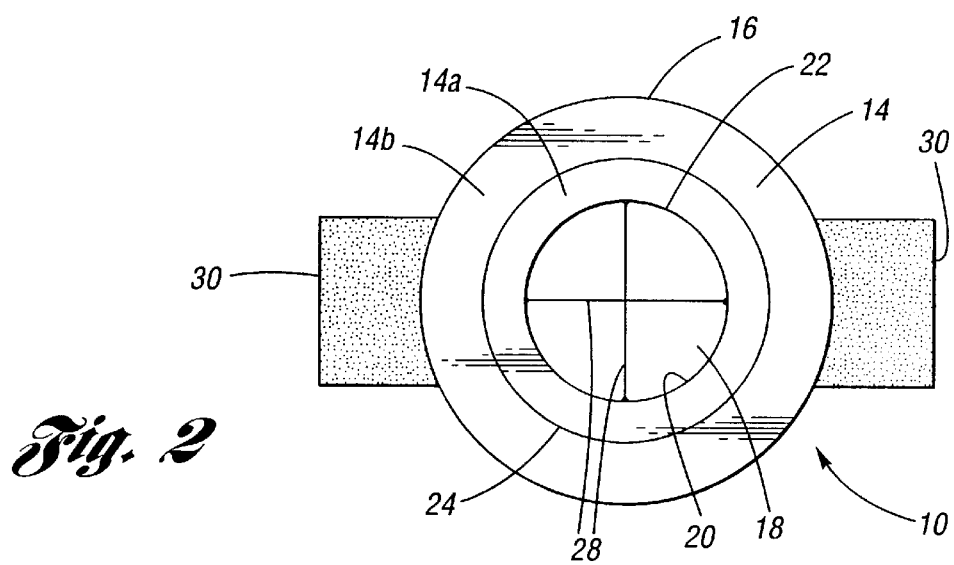
FIG. 2 is a bottom plan view of the ophthalmic instrument, seen along line 2—2 in FIG. 1.

Referring firstly to FIGS. 1 and 2, the ophthalmic instrument 10 according to the present invention will be described.

The ophthalmic instrument 10 includes a base 12 which is preferably barrel shaped, but may be otherwise. The base 12 has a flat abutment face 14 formed at one end thereof. The preferred configuration of the abutment face has a circular outer periphery 16 and a central aperture 18 defined by a circular inner periphery 20.

An inner annular blade 22 and an outer annular blade 24 are provided which are upstandingly connected in perpendicular relation with the abutment face 14. The inner and outer annular blades 22, 24 are preferably integrally formed of the base, but may be provided therewith by any methodology known to the metallurgical arts. For example, the inner and outer annular blades 22, 24 may be independently formed and then fixedly placed by brazing into respective annular slots formed in the abutment face 14. The inner and outer annular blades 22, 24 are of an extremely thin surgical sharpness, rising to a height preferably of about 50 microns above the abutment face 14. The preferred height of the inner and outer annular blades 22, 24 will be discussed further hereinbelow.

The inner annular blade 22 has a diameter of from about 9 mm. to about 9.5 mm. and the outer annular blade 24 has a diameter of about 10.5 mm. In this regard, it is preferred for the inner annular blade 22 to be located adjoining the inner periphery 20. It is further preferred for the outer annular blade 24 to be medially positioned upon the abutment face 14, wherein an inner abutment face 14a is situated between the inner and outer annular blades, and an outer abutment face 14b is located radially outward from the outer annular blade. The surface area of the abutment face 14 is sufficient to prevent the inner and outer annular blades 22, 24 from penetrating a cornea further than their respective height above the abutment face 14, as will be described hereinbelow.

The base 12 has a central hollow 26 which carries therein a cross-hair 28 for sighting the position of the inner and outer annular blades 22, 24 relative to an eye (which procedure will be discussed hereinbelow). The central hollow 26 is aligned with the inner periphery 20 of the abutment face 14.

The base 12 includes preferably (but not necessary) an external handhold 30 for a surgeon to competently grasp the ophthalmic instrument 10 with a high level of skill and exactitude.

The ophthalmic method according to the present invention is performed prior to LASIK and employs the aforesaid ophthalmic instrument 10, as shown at FIGS. 3 through 6.

Figure 3:
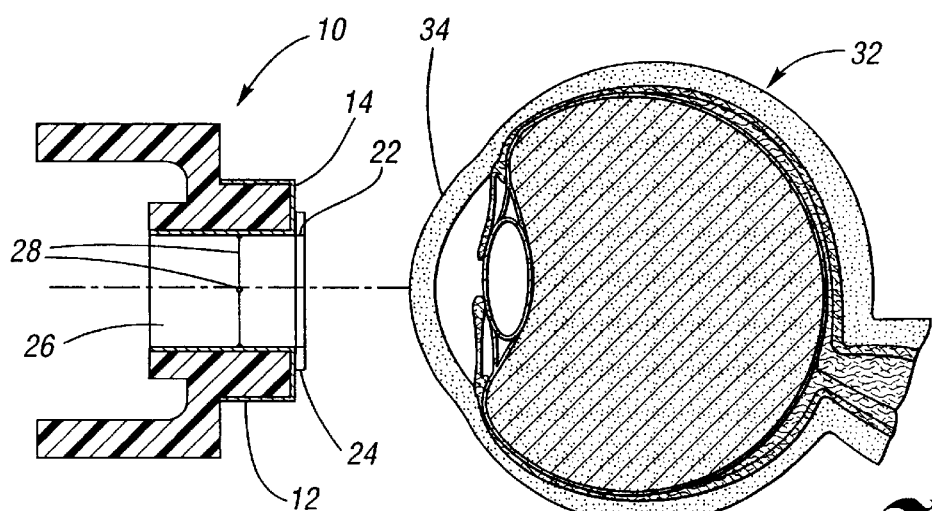
FIG. 3 is a partly cross-sectional view of an ophthalmic instrument according to the present invention, shown in operation with respect to an eye according to the ophthalmic method of the present invention.

As shown at FIG. 3, the ophthalmic instrument 10 is grasped (preferably via the handhold 30) by a surgeon with the inner and outer annular blades 22, 24 facing a patient's eye 32. The surgeon looks through the central hollow 26 and uses the cross-hair 28 to exactly align the inner and outer annular blades over the cornea 34 of the eye 32. The surgeon then presses the ophthalmic instrument 10 upon the eye so that the inner and outer annular blades cut into the cornea until the abutment face abuts the cornea and prevents further penetration. The corneal cutting by the inner and outer annular blades 22, 24 may be provided by simple pressing onto the cornea 34 or pressing accompanied by rotation. The depth of cut of the inner and outer annular blades is such as to completely cut through the epithelium, but preferably without substantially cutting into the stroma.

Figure 4:
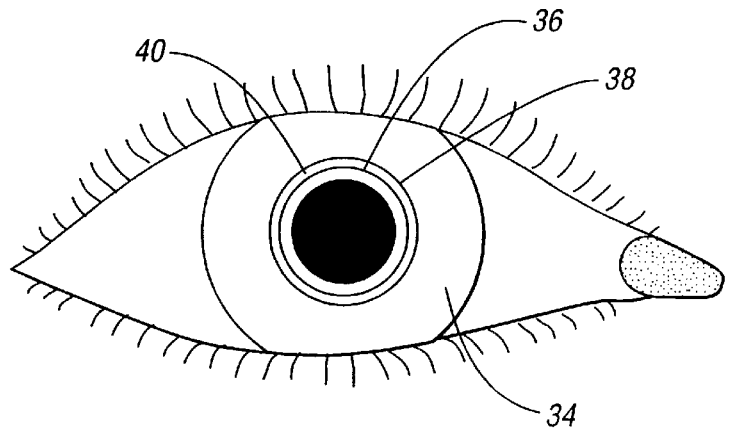
FIG. 4 is a frontal view of the eye of FIG. 3 after completion of use of the ophthalmic instrument in accordance with the ophthalmic method of the present invention.

The surgeon removes the ophthalmic instrument 10 from the eye, and, as shown at FIG. 4, mutually concentric inner and outer annular cuts 36, 38 in the cornea 34 are left behind, an epithelial ring 40 being located therebetween.

Figure 5:
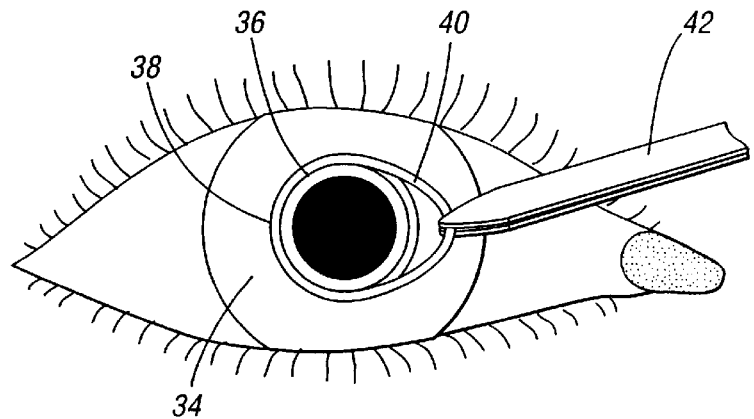
FIG. 5 is a frontal view of the eye of FIG. 4, wherein an epithelial ring is shown being removed therefrom in accordance with the ophthalmic method of the present invention.

Next, as shown at FIG. 5, the surgeon uses an ophthalmic tool 42, such as for example a delicate forceps or tweezers to carefully grasp the epithelial ring 40 and pull it free of the remainder of the cornea 34. As a result, an annular epithelial void 44 is present on the cornea 34, as shown at FIG. 6.

Figure 6:
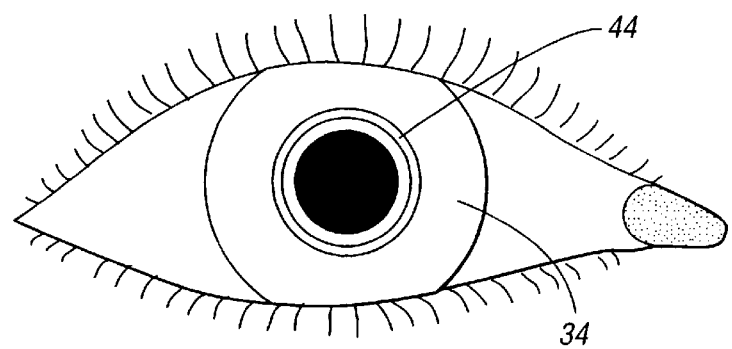
FIG. 6 is a frontal view of the eye of FIG. 5, wherein the epithelial ring has been removed therefrom and the eye is now ready for LASIK in accordance with the ophthalmic method of the present invention.

With an eye prepared with the annular epithelial void 44, as shown at FIG. 6, the surgeon commences LASIK upon the eye. The microkeratome is placed upon the cornea in the usual way known in the medical art, whereby the microkeratome blade is centered on the inner and outer cuts 36, 38 and the microkeratome blade is sized in relation to the diameters of the inner and outer cuts so that when the LASIK flap cut is made in the usual movement of the sliding blade mechanism of the microkeratome, the microkeratome blade does not cut epithelium tissue, it only cuts stroma tissue. The stroma only cutting of the cornea by the microkeratome blade occurs because of the presence of the epithelial void 44 which is located at the perimeter of the flap where the epithelial interface would conventionally have been produced during LASIK. The surgeon then continues on with remaining steps of LASIK.

Accordingly, since there is no epithelium interface produced during the flap cut, there is no chance for errant epithelium cells from being deposited at the stroma interface during LASIK.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. An ophthalmic method for preparing an eye for LASIK comprising the steps of:

cutting an inner annular cut into a cornea at an orientation substantially normal to the cornea;

cutting an outer annular cut into the cornea at an orientation substantially normal to the cornea, wherein the inner and outer annular cuts are mutually concentric substantially parallel to each other and nonintersecting, and wherein an epithelium ring is created therebetween; and removing the epithelium ring.

2. The method of claim 1, wherein said steps of cutting cut fully through the epithelium layer of the cornea.

3. The method of claim 2, wherein said steps of cutting do not substantially cut into the stroma layer of the cornea.

4. The method of claim 2, wherein said step of cutting an inner annular cut provides an inner annular cut diameter of between about nine millimeters and about nine and one half millimeters, and further provides an outer annular cut diameter of about ten and one half millimeters.

5. An ophthalmic method for cutting a corneal flap only through the stroma layer of the cornea, said method comprising the steps of:

cutting an inner annular cut into a cornea;

cutting an outer annular cut into the cornea, wherein the inner and outer annular cuts are mutually concentric, wherein an epithelium ring is created therebetween which fully cuts through the epithelium layer of the cornea, and wherein the the inner and outer annular cuts do not intersect such that the epithelium ring remains attached to the cornea;

removing the epithelium ring to thereby create an epithelial void; and cutting a corneal flap wherein the epithelium void is at the perimeter of the corneal flap so that only the stroma layer is cut.

6. The method of claim 5, wherein said step of cutting an inner annular cut provides an inner annular cut diameter of between about nine millimeters and about nine and one half millimeters, and further provides an outer annular cut diameter of about ten and one half millimeters.

7. An ophthalmic instrument comprising:

a body having a flat abutment face;

an inner annular blade connected to said abutment face in upstanding, perpendicular relationship thereto; and an outer annular blade connected to said abutment face in upstanding, perpendicular relationship thereto, wherein said inner and outer annular blades are mutually concentric.

8. The ophthalmic instrument of claim 7, wherein said inner and outer annular blades have a height of substantially 50 microns with respect to said abutment face.

9. The ophthalmic instrument of claim 8, wherein said inner annular blade has a diameter of substantially between about nine millimeters and nine and one half millimeters; and wherein said outer annular blade has a diameter of substantially ten and one half millimeters.

10. The ophthalmic instrument of claim 9, wherein said abutment face has a central aperture defined by an inner periphery, said inner annular blade adjoining said inner periphery.

11. The ophthalmic instrument of claim 10, wherein said abutment face has an outer periphery, said outer annular blade being substantially medially situated between said inner annular blade and said outer periphery.

12. The ophthalmic instrument of claim 11, further comprising sight means for aligning said inner and outer annular blades with respect to a cornea.

13. The ophthalmic instrument of claim 12, further comprising handhold means for handling said body when aligning said inner and outer annular blades with respect to a cornea.

14. The ophthalmic instrument of claim 7, wherein said abutment face has an outer periphery, said outer annular blade being substantially medially situated between said inner annular blade and said outer periphery.

15. The ophthalmic instrument of claim 14, wherein said abutment face has a central aperture defined by an inner periphery, said inner annular blade adjoining said inner periphery.

16. The ophthalmic instrument of claim 15, wherein said inner and outer annular blades have a height of substantially 50 microns with respect to said abutment face.

17. The ophthalmic instrument of claim 16, wherein said inner annular blade has a diameter of substantially nine millimeters; and wherein said outer annular blade has a diameter of substantially ten and one half millimeters.

* * * * *